United States Patent [19]

Estes et al.

[11] Patent Number: 5,239,995

[45] Date of Patent: Aug. 31, 1993

[54] SLEEP APNEA TREATMENT APPARATUS

[75] Inventors: Mark C. Estes, Irwin; Janice M. Cattano, Gibsonia, both of Pa.

[73] Assignee: Respironics, Inc., Murrysville, Pa.

[21] Appl. No.: 786,269

[22] Filed: Nov. 1, 1991

Related U.S. Application Data

[63] Continuation-in-part of Ser. No. 411,012, Sep. 22, 1989, Pat. No. 5,148,802.

[51] Int. Cl.$^5$ .................. A61M 16/00; A62B 7/00; F16K 31/02
[52] U.S. Cl. .................. 128/204.23; 128/204.21; 128/204.18
[58] Field of Search ............ 128/204.21, 204.23, 128/204.26, 204.18, 419 G, 421, 205.25

[56] References Cited

U.S. PATENT DOCUMENTS

| | | | |
|---|---|---|---|
| 3,961,627 | 6/1976 | Ernst et al. | 128/204.23 |
| 4,570,631 | 2/1986 | Durkan | 128/204.23 |
| 4,776,333 | 10/1988 | Miyamae | 128/204.21 |
| 4,823,788 | 4/1989 | Smith et al. | 128/205.24 |
| 5,117,819 | 6/1992 | Servidio et al. | 128/204.18 |

OTHER PUBLICATIONS

"A Quiet CPAP System...", Lifecare® CPAP-100, Jul. 1991, Form #544, Lafayette, CO, 80026-9341.

Primary Examiner—Edgar S. Burr
Assistant Examiner—Kimberly L. Asher
Attorney, Agent, or Firm—Reed, Smith, Shaw & McClay

[57] ABSTRACT

Improved methodology and apparatus for the treatment of sleep apnea through (1) application of alternating high and low level positive airway pressure within the airway of the patient with the high and low airway pressure being coordinated with the spontaneous respiration of the patient, (2) usage of adjustably programmable pressure ramp circuitry capable of producing multiple pressure ramp cycles of predetermined duration and pattern whereby the ramp cycles may be customized to accommodate the specific needs of an individual sleep apnea patient so as to ease the patient's transition from wakefulness to sleep, and (3) remote control operation of the apparatus for assisting those patients whose mobility or capacity for physical exertion is intrinsically limited.

34 Claims, 8 Drawing Sheets

SLEEP APNEA TREATMENT APPARATUS

CROSS REFERENCE TO RELATED APPLICATION

This application is a continuation-in-part of pending U.S. patent application Ser. No. 07/411,012, filed Sep. 22, 1989, now U.S. Pat. No. 5,148,802 Entitled METHOD FOR TREATMENT OF SLEEP APNEA AND APPARATUS FOR PROVIDING SUCH TREATMENT.

FIELD OF THE INVENTION

The present invention relates generally to methodology and apparatus for treatment to sleep apnea and, more particularly, to mono-level, bi-level, or proportional assist ventilation (PAV) continuous positive airway pressure (CPAP) apparatus including circuitry for enabling a patient to selectively actuate one or more pressure ramp cycles wherein, during each ramp cycle, available airway pressure increases with time from a predetermined minimum pressure value to a prescription pressure, thereby facilitating the patient's transition from a waking to a sleeping state.

BACKGROUND OF THE INVENTION

The sleep apnea syndrome afflicts an estimated 1% to 3% of the general population and is due to episodic upper airway obstruction during sleep. Those afflicted with sleep apnea experience sleep fragmentation and intermittent, complete or nearly complete cessation of ventilation during sleep with potentially severe degrees of oxyhemoglobin unsaturation. These features may be translated clinically into debilitating daytime sleepiness, cardiac dysrhythmias, pulmonary-artery hypertension, congestive heart failure and cognitive dysfunction. Other sequelae of sleep apnea include right ventricular dysfunction with cor pulmonale, carbon dioxide retention during wakefulness as well as during sleep, and continuous reduced arterial oxygen tension. Hypersomnolent sleep apnea patients may be at risk for excessive mortality from these factors as well as by an elevated risk for accidents while driving and/or operating potentially dangerous equipment.

Although details of the pathogenesis of upper airway obstruction in sleep apnea patients have not been fully defined, it is generally accepted that the mechanism includes either anatomic or functional abnormalities of the upper airway which result in increased air flow resistance. Such abnormalities may include narrowing of the upper airway due to suction forces evolved during inspiration, the effect of gravity pulling the tongue back to appose the pharyngeal wall, and/or insufficient muscle tone in the upper airway dilator muscles. It has also been hypothesized that a mechanism responsible for the known association between obesity and sleep apnea is excessive soft tissue in the anterior and lateral neck which applies sufficient pressure on internal structures to narrow the airway.

The treatment of sleep apnea has included such surgical interventions as uvulopalatopharyngoplasty, gastric surgery for obesity, and maxillo-facial reconstruction. Another mode of surgical intervention used in the treatment of sleep apnea is tracheostomy. These treatments constitute major undertakings with considerable risk of postoperative morbidity if not mortality. Pharmacologic therapy has in general been disappointing, especially in patients with more than mild sleep apnea. In addition, side effects from the pharmacologic agents that have been used are frequent. Thus, medical practitioners continue to seek non-invasive modes of treatment for sleep apnea with high success rates and high patient compliance including, for example in cases relating to obesity, weight loss through a regimen of exercise and regulated diet.

Recent work in the treatment of sleep apnea has included the use of continuous positive airway pressure (CPAP) to maintain the airway of the patient in a continuously open state during sleep. For example, U.S. Pat. No. 4,655,213 and Australian patent AU-B-83901/82 both disclose sleep apnea treatments based on continuous positive airway pressure applied within the airway of the patient.

Also of interest is U.S. Pat. No. 4,773,411 which discloses a method and apparatus for ventilatory treatment characterized as airway pressure release ventilation and which provides a substantially constant elevated airway pressure with periodic short term reductions of the elevated airway pressure to a pressure magnitude no less than ambient atmospheric pressure.

Published PCT Application No. WO 88/10108 describes a CPAP apparatus which includes a feedback system for controlling the output pressure of a variable pressure air source whereby output pressure from the air source is increased in response to detection of sound indicative of snoring. A pressure ramp cycle (i.e., a gradual increase in output pressure) occurs upon initial activation of the apparatus while other ramp cycles occur automatically thereafter upon detection of snoring sounds from the patient.

Publications pertaining to the application of CPAP in treatment of sleep apnea include the following:

1. Lindsay, DA, Issa FG, and Sullivan C. E. "Mechanisms of Sleep Desaturation in Chronic Airflow Limitation Studied with Nasal Continuous Positive Airway Pressure (CPAP), " *Am Rev Respir Dis,* 1982; 125: p. 112.
2. Sanders NH, Moore SE, Eveslage J. "CPAP via nasal mask: A treatment for occlusive sleep apnea, *Chest,* 1983; 83: pp. 144–145.
3. Sullivan CE, Berthon-Jones M. Issa FG. "Remission severe obesity-hypoventilation syndrome after short-term treatment during sleep with continuous positive airway pressure, *Am Rev Respir Dis,* 1983; 128: pp. 177–181.
4. Sullivan CE, Issa FG, Berthon-Jones M., Eveslage J. "Reversal of obstructive sleep apnea by continuous positive airway pressure applied through the nares, *Lancet,* 1981; 1: pp. 862–865.
5. Sullivan CE, Berthon-Jones M. Issa FG. "Treatment of obstructive apnea with continuous positive airway pressure applied through the nose. *Am Rev Respir Dis,* 1982; 125: p. 107. Annual Meeting Abstracts.
6. Rapoport DM, Sorkin B, Garay SM, Goldring RN. "Reversal of the 'Pickwickian Syndrome' by long-term use of nocturnal nasal-airway pressure," *N Engl J. Med,* 1982; 307: pp. 931–933.
7. Sanders MH, Holzer BC, Pennock BE. "The effect of nasal CPAP on various sleep apnea patterns, *Chest,* 1983; 84: p. 336. Presented at the Annual Meeting of the American College of Chest Physicians, Chicago Ill., October 1983.
8. Sanders, MH. "Nasal CPAP Effect on Patterns of Sleep Apnea", *Chest,* 1984; 86: 839–844.

Although CPAP has been found to be very effective and well accepted, it suffers from some of the same limitations, although to a lesser degree, as do the surgery options; specifically a significant proportion of sleep apnea patients do not tolerate CPAP well. Thus, development of other viable non-invasive therapies has been a continuing objective in the art.

SUMMARY OF THE INVENTION

The present invention contemplates a novel and improved method for treatment of sleep apnea as well as novel methodology and apparatus for carrying out such improve treatment method. The invention contemplates the treatment of sleep apnea through application of pressure at variance with ambient atmospheric pressure within the upper airway of the patient in a manner to promote dilation of the airway to thereby relieve upper airway occlusion during sleep.

In a first embodiment of the invention, positive pressure is applied at a substantially constant pressure within the airway of the patient to maintain the requisite dilating force to sustain respiration during sleep periods. This form of treatment is commonly known as mono-level CPAP therapy.

In another embodiment of the invention, positive pressure is applied alternately at relatively higher and lower pressure levels within the airway of the patient so that the pressure-induced force applied to dilate the patients airway is alternately a larger and a smaller magnitude dilating force. The higher and lower magnitude positive pressures are initiated by spontaneous patient respiration with the higher magnitude pressure being applied during inspiration and the lower magnitude pressure being applied during expiration. This method of treatment may descriptively be referred to as bi-level CPAP therapy.

The invention further contemplates a novel and improved apparatus which is operable in accordance with a novel and improved method to provide sleep apnea treatment. More specifically, a flow generator and an adjustable pressure controller supply air flow at a predetermined, adjustable pressure to the airway of a patient through a flow transducer. The flow transducer generates an output signal which is then conditioned to provide a signal proportional to the instantaneous flow rate of air to the patient. The instantaneous flow rate signal is fed to a low pass filter which passes only a signal indicative of the average flow rate over time. The average flow rate signal typically would be expected to be a value representing a positive flow as the system is likely to have at least minimal leakage from the patient circuit (e.g., small leaks about the perimeter of the respiration mask worn by the patient). The average flow signal is indicative of such leakage because the summation of all other components of flow over time must be essentially zero since inspiration flow must equal expiration flow volume over time, that is, over a period of time the volume of air breathed in equals the volume of the gases breathed out.

Both the instantaneous flow signal and the average flow rate signal are fed to an inspiration/ expiration decision module which is, in its simplest form, a comparator that continually compares the input signals and provides a corresponding drive signal to the pressure controller. In general, when the instantaneous flow exceeds average flow, the patient is inhaling and the drive signal supplied to the pressure controller sets the pressure controller to deliver air, at a preselected elevated pressure, to the airway of the patient. Similarly, when the instantaneous flow rate is less than the average flow rate, the patient is exhaling and the decision circuitry thus provides a drive signal to set the pressure controller to provide a relatively lower magnitude of pressure in the airway of the patient. The patient's airway thus is maintained open by alternating higher and lower magnitudes of pressure which are applied during spontaneous inhalation and exhalation, respectively.

As has been noted, some sleep apnea patients do not tolerate standard CPAP therapy. Specifically, approximately 25% of patients cannot tolerate CPAP due to the attendant discomfort. CPAP mandates equal pressures during both inhalation and exhalation. The elevated pressure during both phases of breathing may create difficulty in exhaling and the sensation of an inflated chest. However, we have determined that although both inspiratory and expiratory air flow resistances in the airway are elevated during sleep preceding the onset of apnea, the airway flow resistance may be less during expiration than during inspiration. Thus it follows that the bi-level CPAP therapy of our invention as characterized above may be sufficient to maintain pharyngeal patency during expiration even though the pressure applied during expiration is not as high as that needed to maintain pharyngeal patency during inspiration. In addition, some patients may have increased upper airway resistance primarily during inspiration with resulting adverse physiologic consequences. Thus, our invention also contemplates applying elevated pressure only during inhalation thus eliminating the need for global (inhalation and exhalation) increases in airway pressure. The relatively lower pressure applied during expiration may in some cases approach or equal ambient pressure. The lower pressure applied in the airway during expiration enhances patient tolerance by alleviating some of the uncomfortable sensations normally associated with CPAP.

Under prior CPAP therapy, pressures as high as 15 cm $H_2O$ have been required, and some patients on nasal CPAP thus have been needlessly exposed to unnecessarily high expiratory pressures with the attendant discomfort and elevated mean airway pressure, and theoretic risk of barotrauma. Our invention permits independent application of a higher inspiratory airway pressure in conjunction with a lower expiratory airway pressure in order to provide a therapy which is better tolerated by the 25% of the patient population which does net tolerate CPAP therapy, and which may be safer in the other 75% of the patient population.

As has been noted hereinabove, the switch between higher and lower pressure magnitudes can be controlled by spontaneous patient respiration, and the patient thus is able to independently govern respiration rate and volume. As has been also noted, the invention contemplates automatic compensation for system leakage whereby nasal mask fit and air flow system integrity are of less consequence than in the prior art. In addition to the benefit of automatic leak compensation, other important benefits of the invention include lower mean airway pressures for the patient and enhanced safety, comfort and tolerance.

In all embodiments, the present invention makes use of "ramp" circuitry operatively connected to pressure control means of the CPAP apparatus and selectively activatable by the patient to effect at least one pressure "ramp cycle" which is described in greater detail below. The maximum duration of the ramp cycle, the shape of the ramp curve and the prescription pressure are normally established by a sleep study of the patient and this data can be programmed into the CPAP apparatus of the instant invention. It is also desirable that the CPAP apparatus be operable either by manual controls located directly on the apparatus or via remote control.

Approximately 25% of all patients who undergo CPAP therapy for sleep apnea experience respiration discomfort and find it difficult to fall asleep because of the therapy. The purpose of a ramp cycle is to alleviate this discomfort. A ramp cycle is an automatic cycle that, once activated, causes the CPAP apparatus to output a predetermined minimum positive pressure at or above ambient pressure which is gradually increased over a predetermined time period known as "ramp time" during which the patient begins to fall asleep. Upon expiration of the ramp time the patient typically has fallen asleep and at such time the pressure produced by the apparatus is that of the patient's CPAP therapy prescription pressure whereupon the patient receives normal CPAP treatment as he sleeps.

A particular advantage of the present invention is that the unique ramp circuitry enables not only an initial ramp cycle to be achieved for when one first attempts to sleep but such circuitry also permits one or more additional cycles to be selectively activated by the user at instances where the user awakens during an extended rest period and again requires a ramp cycle to fall back to sleep. Typically, during a sleeping period of several hours, the time required to once again fall asleep after briefly being awakened is generally less than the time spent initially falling asleep. To accommodate this phenomenon, the ramp circuitry of the instant invention allows the user to advantageously adjust the ramp time of any additional ramp cycle to run for a selected fraction of the initial ramp time, which itself is a patient-selected fraction of a prescription pressure preset by a health care professional in supervision of the patient's sleep apnea treatment.

The ramp circuitry enables a physician or other health care worker to set the initial ramp time and prescription pressure. Additionally, however, the novel ramp circuitry of the present invention permits adjustment of the "shape" of the pressure ramp curve, whereby the physician, health care worker or patient can suitably manipulate appropriate controls associated with the ramp circuitry to control the pressure output pattern of the ramp (as represented as a function of pressure versus time) such that it may assume virtually any configuration including, inter alia, linear, stepped, or curvilinear slope, depending upon a patient's particular needs as dictated by the results of the patient's sleep study.

Additionally, sufferers of sleep apnea are sometimes afflicted by other maladies which limit the degree to which they may safely physically exert themselves. An advantage of the present invention is that it enables a limited-mobility user, at his discretion, to operate the CPAP apparatus either by manual controls located directly on the apparatus or via remote control. Equally as important, it provides any sleep apnea sufferer using the CPAP apparatus with the peace of mind of knowing that the pressure can be reduced at any time via the remote control. Further, the preferred embodiment of the remote control contemplated for use in the present invention is one which the user can operate easily and reliably either in light or darkness to turn the apparatus on and off as well as selectively activate the first or subsequent ramp cycles.

Further, although the ramp circuitry discussed hereinbelow will be described specifically in connection with mono-level and bi-level CPAP apparatus, it will be understood that its utility and applicability is not limited thereto. That is to say, within the scope of the instant invention it is also contemplated that the presently disclosed ramp circuitry may be incorporated into other types of CPAP apparatus including, but not limited to, proportional assist ventilation (PAV) devices which are similar to bi-level CPAP devices but instead provide substantially continuous adjustment of pressure in response to patent volume and flow instead of alternating between two fixed pressures in response to flow.

Other details, objects and advantages of the present invention will become apparent as the following description of the presently preferred embodiments and presently preferred methods of practicing the invention proceeds.

BRIEF DESCRIPTION OF THE DRAWINGS

The invention will become more readily apparent from the following description of preferred embodiments thereof shown, by way of example only, in the accompanying drawings, wherein.

DETAILED DESCRIPTION OF THE INVENTION

Figure 1:
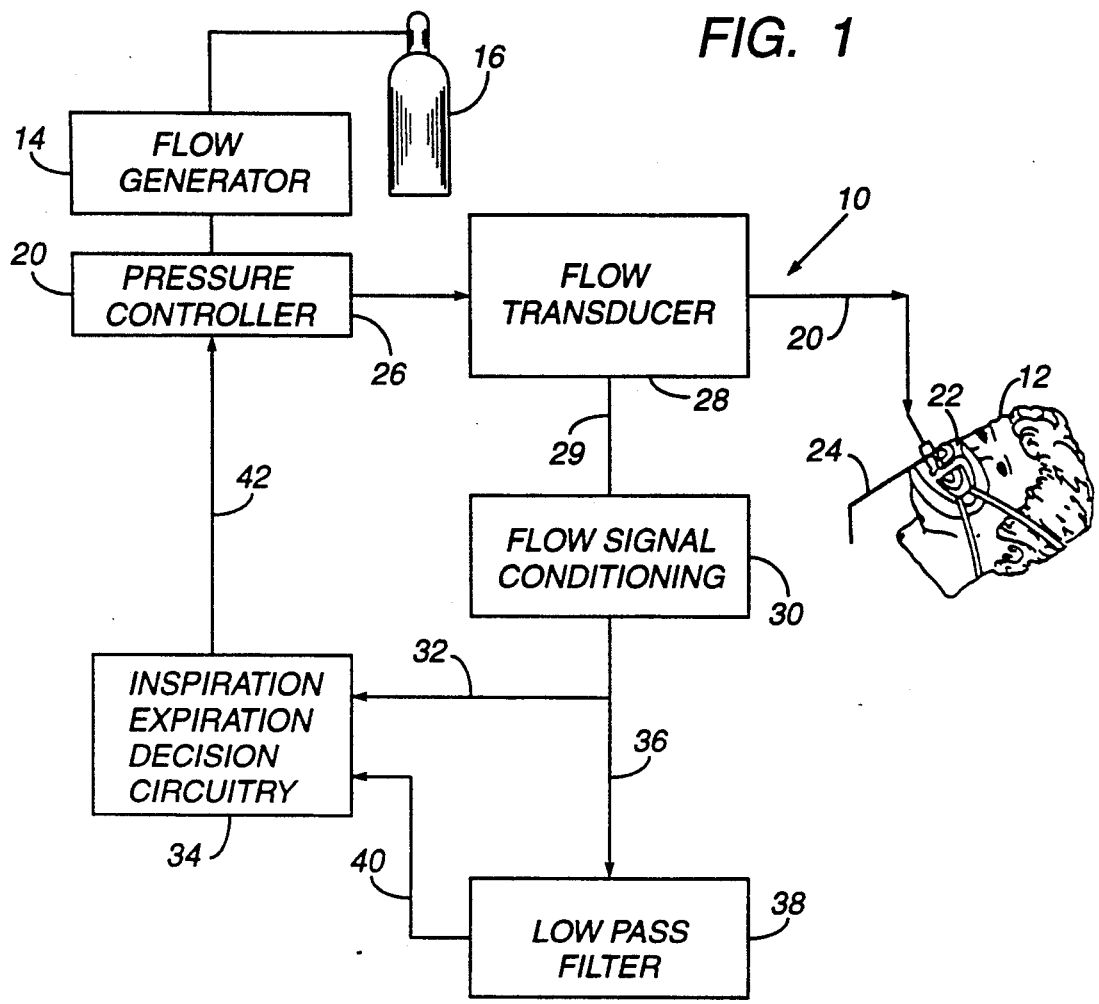
FIG. 1 is a functional block diagram of an apparatus according to the instant invention.

There is generally indicated at 10 in FIG. 1 an apparatus according to one presently preferred embodiment of the instant invention and shown in the form of a functional block diagram. Apparatus 10 is operable according to a novel process which is another aspect of the instant invention for delivering breathing gas such as air alternately at relatively higher and lower pressures (i.e., equal to or above ambient atmospheric pressure) to a patient 12 for treatment of the condition known as sleep apnea.

Apparatus 10 comprises a gas flow generator 14 (e.g., a blower) which receives breathing gas from any suitable source, a pressurized bottle 16 or the ambient atmosphere, for example. The gas flow from flow generator 14 is passed via a delivery conduit 20 to a breathing appliance such as a mask 22 of any suitable known construction which is worn by patient 12. The mask 22 may preferably be a nasal mask or a full face mask 22 as shown. Other breathing appliances which may be used in lieu of a mask include nasal cannulae, an endotracheal tube, or any other suitable appliance for interfacing between a source of breathing gas and a patient.

The mask 22 includes a suitable exhaust port means, schematically indicated at 24, for exhaust of breathing gases during expiration. Exhaust port 24 preferably is a continuously open port which imposes a suitable flow resistance upon exhaust gas flow to permit a pressure controller 26, located in line with conduit 20 between flow generator 14 and mask 22, to control the pressure of air flow within conduit 20 and thus within the airway of the patient 12. For example, exhaust port 24 may be of sufficient cross-sectional flow area to sustain a continuous exhaust flow of approximately 15 liters per minute. The flow via exhaust port 24 is one component, and typically the major component of the overall system leakage, which is an important parameter of system operation. In an alternative embodiment to be discussed hereinbelow, it has been found that a non-rebreathing valve may be substituted for the continuously open port 24.

The pressure controller 26 is operative to control the pressure of breathing gas within the conduit 20 and thus within the airway of the patient. Pressure controller 26 is located preferably, although not necessarily, downstream of flow generator 14 and may take the form of an adjustable valve which provides a flow path which is open to the ambient atmosphere via a restricted opening, the valve being adjustable to maintain a constant pressure drop across the opening for all flow rates and thus a constant pressure within conduit 20.

Also interposed in line with conduit 20, preferably downstream of pressure controller 26, is a suitable flow transducer 28 which generates an output signal that is fed as indicated at 29 to a flow signal conditioning circuit 30 for derivation of a signal proportional to the instantaneous flow rate of breathing gas within conduit 20 to the patient.

It will be appreciated that flow generator 14 is not necessarily a positive displacement device. It may be, for example, a blower which creates a pressure head within conduit 20 and provides air flow only to the extent required to maintain that pressure head in the presence of patient breathing cycles, the exhaust opening 24, and action of pressure controller 26 as above described. Accordingly, when the patient is exhaling, peak exhalation flow rates from the lungs may far exceed the flow capacity of exhaust port 24. As a result, exhalation gas back flows within conduit 20 through flow transducer 28 and toward pressure controller 26, and the instantaneous flow rate signal from transducer 28 thus will vary widely within a range from relatively large positive (i.e., toward the patient) flow to relatively large negative (i.e., from the patient) flow.

The instantaneous flow rate signal from flow signal conditioning circuitry 30 is fed as indicated at 32 to a decision module 34, a known comparator circuit for example, and is additionally fed as indicated at 36 to a low pass filter 38. Low pass filter 38 has a cutoff frequency low enough to remove from the instantaneous flow rate input signal most variations in the signal which are due to normal breathing. Low pass filter 38 also has a long enough time constant to ensure that spurious signals, aberrant flow patterns and peak instantaneous flow rate values will not dramatically affect system average flow. That is, the time constant of low pass filter 38 is selected to be long enough that it responds slowly to the instantaneous flow rate signal input. Accordingly, most instantaneous flow rate input signals which could have a large impact on system average flow in the short term have a much smaller impact over a longer term, largely because such instantaneous flow rate signal components will tend to cancel over the longer term. For example, peak instantaneous flow rate values will tend to be alternating relatively large positive and negative flow values corresponding to peak inhalation and exhalation flow achieved by the patient during normal spontaneous breathing. The output of low pass filter 38 thus is a signal which is proportional to the average flow in the system, and this is typically a positive flow which corresponds to average system leakage (including flow from exhaust 24) since, as noted, inhalation and exhalation flow cancel for all practical purposes.

The average flow signal output from the low pass filter 38 is fed as indicated at 40 to decision circuitry 34 where the instantaneous flow rate signal is continually compared to the system average flow signal. The output of the decision circuitry 34 is fed as a drive signal indicated at 42 to control the pressure controller 26. The pressure magnitude of breathing gas within conduit 20 thus is coordinated With the spontaneous breathing effort of the patient 12, as follows.

When the patient begins to inhale, the instantaneous flow rate signal goes to a positive value above the positive average flow signal value. Detection of this increase in decision circuitry 34 is sensed at the start of patient inhalation. The output signal from decision circuitry 34 is fed to pressure controller 26 which, in response, provides higher pressure gas flow within conduit 20 and thus higher pressure within the airway of the patient 12. This is the higher magnitude pressure value of our bi-level CPAP system and is referred to hereinbelow as IPAP (inhalation positive airway pressure). During inhalation, the flow rate within conduit 20 will increase to a maximum and then decrease as inhalation comes to an end.

At the start of exhalation, air flow into the patient's lungs is nil and as a result the instantaneous flow rate signal will be less than the average flow rate signal which, as noted is a relatively constant positive flow value. The decision circuitry 34 senses this condition at the start of exhalation and provides a drive signal to pressure controller 26 which, in response, provides gas flow within conduit 20 at a lower pressure which is the lower magnitude pressure value of the bi-level CPAP system, referred to hereinbelow as EPAP (exhalation positive airway pressure). As has been noted hereinabove the range of EPAP pressures may include ambient atmospheric pressure. When the patient again begins spontaneous inhalation, the instantaneous flow rate signal again increases over the average flow rate signal, and the decision circuitry once again feeds a drive signal to pressure controller 26 to reinstitute the IPAP pressure.

System operation as above specified requires at least periodic comparison of the input signals 32 and 40 by decision circuitry 34. Where this or other operations are described herein as continual, the scope of meaning to be ascribed includes both continuous (i.e., uninterrupted) or periodic (I.e., at discrete intervals).

As has been noted, the system 10 has a built-in controlled leakage via exhaust port 24 thus assuring that the average flow signal will be at least a small positive flow. During inhalation, the flow sensed by the flow transducer will be the sum of exhaust flow via port 24 and all other system leakage downstream of transducer 28, and inhalation flow within the airway of the patient 12. Accordingly, during inhalation the instantaneous flow rate signal as conditioned by conditioning module 30, will reliably and consistently reflect inhalation flow exceeding the average flow rate signal. During exhalation, the flow within conduit 20 reverses as exhalation flow from the lungs of the patient far exceeds the flow capacity of exhaust port 24. Accordingly, exhalation air backflows within conduit 20 past transducer 28 and toward pressure controller 26. Since pressure controller 26 is operable to maintain set pressure, it will act in response to flow coming from both the patient and the flow generator to open an outlet port sufficiently to accommodate the additional flow volume and thereby maintain the specified set pressure as determined by action of decision circuitry 34.

In both the inhalation and exhalation cycle phases, the pressure of the gas within conduit 20 exerts a pressure within the airway of the patient to maintain an open airway and thereby alleviate airway constriction.

In practice, it may be desirable to provide a slight offset in the switching level within decision circuitry 34 with respect to the average flow rate signal, so that the system does not prematurely switch from the low pressure exhalation mode to the higher pressure inhalation mode. That is, a switching setpoint offset in the positive direction from system average flow may be provided such that the system will not switch to the IPAP mode until the patient actually exerts a significant spontaneous inspiratory effort of a minimum predetermined magnitude. This will ensure that the initiation of inhalation is completely spontaneous and not forced by an artificial increase in airway pressure. A similar switching setpoint offset may be provided when in the IPAP mode to ensure the transition to the lower pressure EPAP mode will occur before the flow rate of air into the lungs of the patient reaches zero (i.e., the switch to EPAP occurs slightly before the patient ceases inhalation.) This will ensure that the patient will encounter no undue initial resistance to spontaneous exhalation.

From the above description, it will be seen that a novel method of treating sleep apnea is proposed according to which the airway pressure of the patient is maintained at a higher positive pressure during inspiration and a relatively lower pressure during expiration, all without interference with the spontaneous breathing of the patient. The described apparatus is operable to provide such treatment for sleep apnea patients by providing a flow of breathing gas to the patient at positive pressure, and varying the pressure of the air flow to provide alternately high and low pressure within the airway of the patient coordinated with the patient's spontaneous inhalation and exhalation.

To provide pressure control, the flow rate of breathing gas to the patient is detected and processed to continually provide a signal which is proportional to the instantaneous breathing gas flow rate in the system. The instantaneous flow rate signal is further processed to eliminate variations attributable to normal patient respiration and other causes thus generating a signal which is proportional to the average or steady state system gas flow. The average flow signal is continually compared with the instantaneous flow signal as a means to detect the state of the patient's spontaneous breathing versus average system flow. When instantaneous flow exceeds the average flow, the patient is inhaling, and in response the pressure of gas flowing to the patient is set at a selected positive pressure, to provide a corresponding positive pressure within the airway of the patient. When comparison of the instantaneous flow rate signal with the average flow signal indicates the patient is exhaling, as for example when the instantaneous flow signal indicates flow equal to or less than the average flow, the pressure of breathing gas to the patient is adjusted to a selected lower pressure to provide a corresponding lower pressure within the airway of the patient.

Figure 2:
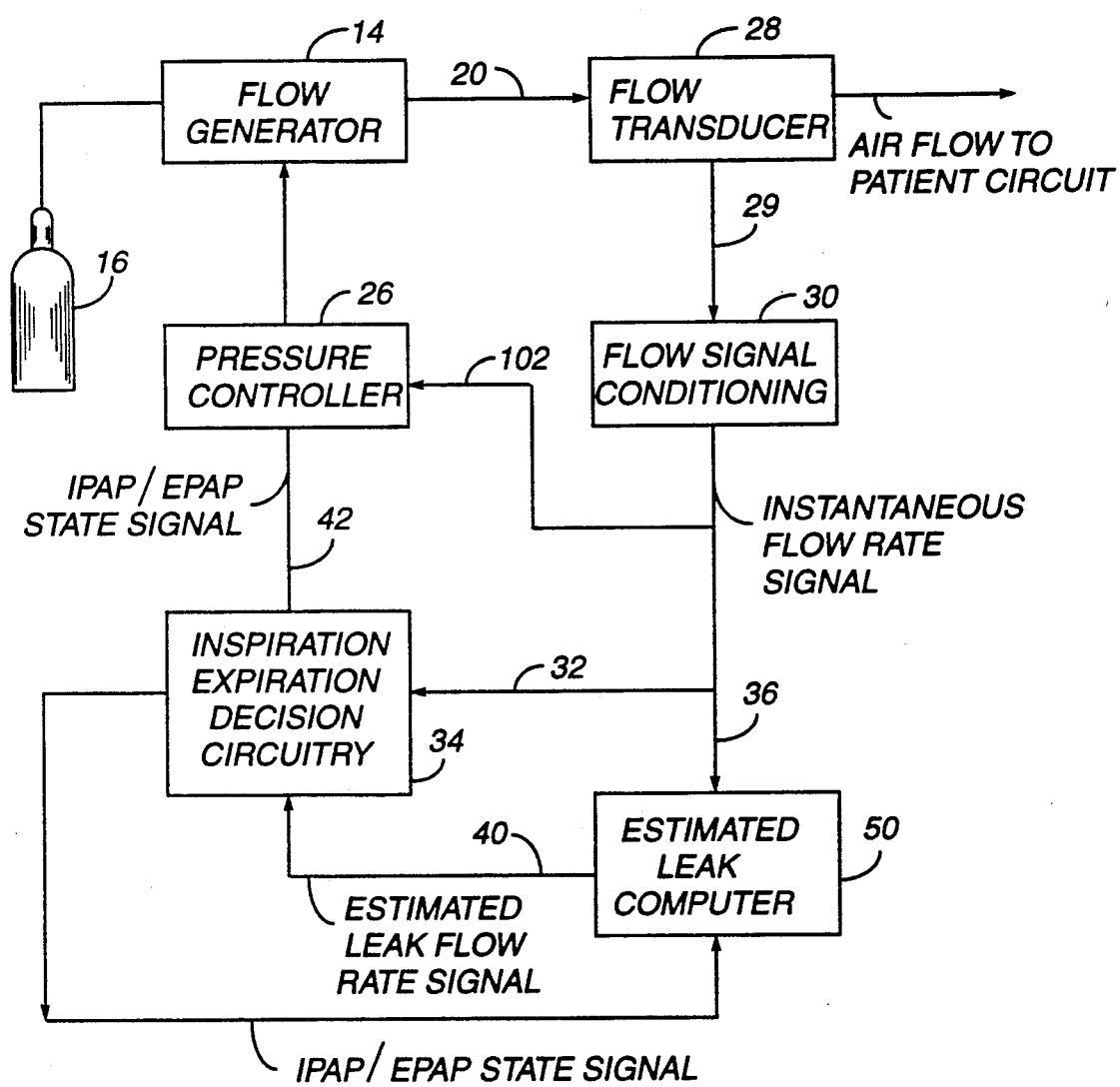
FIG. 2 is a functional block diagram showing an alternative embodiment of the invention.
Figure 3:
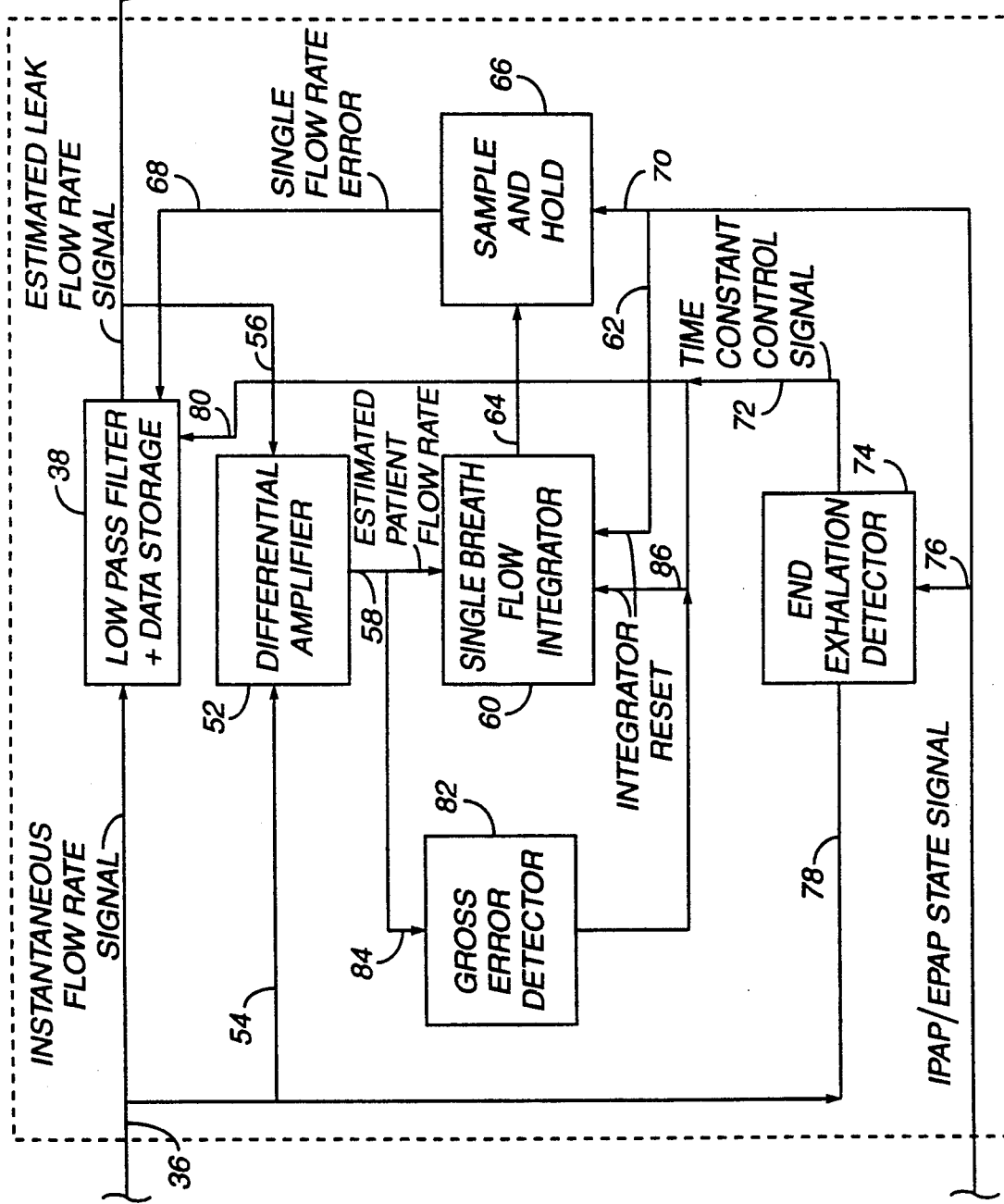
FIG. 3 is a functional block diagram of the Estimated Leak Computer of FIG. 2.

In an alternative embodiment of the invention as shown in FIGS. 2 and 3, the low pass filter 38 is replaced by an estimated leak computer which includes a low pass filter as well as other functional elements as shown in FIG. 3. The remainder of the system as shown in FIG. 2 is similar in most respects to the system shown in FIG. 1. Accordingly, like elements are identified by like numbers, and the description hereinabove of FIG. 1 embodiment also applies generally to FIG. 2.

By using the operative capability of the estimated leak computer 50, as described hereinbelow, it is possible to adjust the reference signal which is fed to decision circuitry 34 on a breath by breath basis rather than merely relying on long term average system flow. To distinguish this new reference signal from average system flow it will he referred to hereinbelow as the estimated leak flow rate signal or just the estimated leak signal.

As was noted hereinabove, the average system flow rate reference signal changes very slowly due to the long time constant of the low pass filter 38. This operative feature was intentionally incorporated to avoid disturbance of the reference signal by aberrant instantaneous flow rate signal inputs such as erratic breathing patterns. While it was possible to minimize the impact of such aberrations on the average flow rate reference signal, the average flow signal did nevertheless change, although by small increments and only very slowly in response to disturbances. Due to the long time constant of the low pass filter, such changes in the reference signal even if transitory could last for a long time.

Additionally, even a small change in the reference signal could produce a very significant effect on system triggering. For example, since the objective is to trigger the system to the IPAP mode when inhalation flow just begins to go positive, small changes in the reference signal could result in relatively large changes in the breathing effort needed to trigger the system to IPAP mode. In some instances the change in reference signal could be so great that with normal breathing effort the patient would be unable to trigger the system. For example, if the system were turned on before placement of the mask an the face of the patient, the initial free flow of air from the unattached mask could result in a very large magnitude positive value for initial average system flow. If such value were to exceed the maximum inspiratory flow rate achieved in spontaneous respiration by the patient, the system would never trigger between the IPAP and EPAP modes because the decision circuitry would never see an instantaneous flow rate signal greater than the average flow rate signal, at least not until a sufficient number of normal breathing cycles after application of the mask to the patient to bring the reference signal down to a value more closely commensurate with the actual system leak in operation. As has been noted, with the low pass filter this could take a rather long time, during which time the patient would be breathing spontaneously against a uniform positive pressure. This would be tantamount to conventional CPAP and not at all in keeping with the present invention.

In addition to the embodiment based on a reference signal derived from estimated leak flow rate on a breath by breath basis which is controlled totally by spontaneous patient breathing, two further modes of operation also are envisioned, one being spontaneous/timed operation in which the system automatically triggers to the IPAP mode for just long enough to initiate patient inspiration if the system does not sense inspiratory effort within a selected time after exhalation begins. To accomplish this, a timer is provided which is reset at the beginning of each patient inspiration whether the inspiratory cycle was triggered spontaneously or by the timer itself. Thus, only the start of inspiration is initiated by the timer. The rest of the operating cycle in this mode is controlled by spontaneous patient breathing and the circuitry of the system to be described.

A further mode of operation is based purely on timed operation of the system rather than on spontaneous patient breathing effort, but with the timed cycles coordinated to spontaneous patient breathing.

Referring to FIG. 3, the estimated leak computer 50 includes the low pass filter 38' as well as other circuits which are operative to make corrections the estimated leak flow rate signal based on ongoing analysis of each patient breath. A further circuit is provided which is operative to adjust the estimated leak flow rate signal quickly after major changes in system flow such as when the blower has been running prior to the time when the mask is first put on the patient, or after a major leak the system has either started or has been shut off.

The low pass filter 38' also includes a data storage capability whose function will be described hereinbelow.

The low pass filter 38' operates substantially as described above with reference to FIG. 1 in that it provides a long term average of system flow which is commensurate with steady state system leakage including the flow capacity of the exhaust port 24. This long term average is operative in the FIG. 3 embodiment to adjust the estimated leak flow rate reference signal only when system flow conditions are changing very slowly.

To provide breath by breath analysis and adjustment of the reference signal, a differential amplifier 52 receives the instantaneous flow rate signal as indicated at 54, and the estimated leak signal output from low pass filter 38' as indicated at 56.

The output of differential amplifier 52 is the difference between instantaneous flow rate and estimated leak flow rate, or in other words estimated instantaneous patient flow rate. This will be clear upon considering that instantaneous flow is the sum of patient flow plus actual system leakage. The estimated patient flow signal output from differential amplifier 52 is provided as indicated at 58 to a flow integrator 60 which integrates estimated patient flow breath by breath beginning and ending with the trigger to IPAP. Accordingly, an additional input to the flow integrator 60 is the IPAP/EPAP state signal as indicated at 62. The IPAP/EPAP state signal is the same as the drive signal provided to pressure controller 26; that is, it is a signal indicative of the pressure state, as between IPAP and EPAP, of the system. The state signal thus may be used to mark the beginning and end of each breath for purposes of breath by breath integration by integrator 60.

If the estimated leak flow rate signal from low pass filter 38' is equal to the true system leak flow rate, and if the patient's inhaled and exhaled volumes are identical for a given breath (i.e., total positive patient flow equals total negative patient flow for a given breath), then the integral calculated by integrator 60 will be zero and no adjustment of estimated leak flow rate will result. When the integral calculated by integrator 60 is nonzero, the integral value in the form of an output signal from integrator 60 is provided as indicated at 64 to a sample and hold module 66. Of course, even with a zero value integral, an output signal may be provided to module 66, but the ultimate result will be no adjustment of the estimated leak flow rate signal.

A nonzero integral value provided to module 66 is further provided to module 38' as indicated at 68 with each patient breath by operative action of the IPAP/EPAP state signal upon module 66 as indicated at 70. The effect of a nonzero integral value provided to module 38' is an adjustment of the estimated leak flow rate signal proportional to the integral value and in the direction which would reduce the integral value towards zero on the next breath if all other conditions remain the same.

With this system, if the patient's net breathing cycle volume is zero, and if the system leak flow rate changes, the integrator circuit will compensate for the change in leak flow rate by incremental adjustments to the estimated leak flow rate within about ten patient breaths.

The integrator circuit 60 also will adjust the estimated leak flow rate signal in response to nonzero net volume in a patient breathing cycle. It is not unusual for a patient's breathing volume to be nonzero. For example, a patient may inhale slightly more on each breath than he exhales over several breathing cycles, and then follow with a deeper or fuller exhalation. In this case, the integrator circuit would adjust the estimated leak flow rate signal as if the actual system leak rate had changed; however, since the reference signal correction is only about one tenth as large as would be required to make the total correction in one breath, the reference signal wild not change appreciably over just one or two breaths. Thus, the integrator circuit accommodates both changes in system leakage and normal variations in patient breathing patterns. The integrator circuit normally would be active, for example, during rapid patient breathing.

An end exhalation module 74 is operative to calculate another data component for use in estimating the system leak flow rate as follows. The module 74 monitors the slope of the instantaneous flow rate wave form. When the slope value is near zero during exhalation (as indicated by the state signal input 76) the indication is that the flow rate is not changing. If the slope of the instantaneous flow rate signal wave form remains small after more than one second into the respiratory phase, the indication is that exhalation has ended and that the net flow rate at this point thus is the leak flow rate. However, if estimated patient flow rate is nonzero at the same time, one component of the instantaneous flow rate signal must be patient flow.

When these conditions are met, the circuit adjusts the estimated leak flow rate slowly in a direction to move estimated patient flow rate toward zero to conform to instantaneous patient flow conditions expected at the end of exhalation. The adjustment to estimated leak flow rate is provided as an output from module 74 to low pass filter 38' as indicated at 80. When this control mechanism takes effect, it disables the breath by breath volume correction capability of integrator circuit 60 for that breath only.

The output of module 74 is a time constant control signal which is provided to low pass filter 38' to temporarily shorten the time constant thereof for a sufficient period to allow the estimated leak flow rate to approach the instantaneous flop rate signal at that specific instant. It will be noted that shortening the low pass filter time constant increases the rapidity with which the low pass filter output (a system average) can adjust toward the instantaneous flow rate signal input.

Another component of estimated leak flow rate control is a gross error detector 82 which acts when the estimated patient flow rate, provided thereto as indicated at 84, is away from zero for more than about 5 seconds. Such a condition may normally occur, for example, when the Flow generator 14 is running before mask 22 is applied to the patient. This part of the control system is operative to stabilize operation quickly after major changes in the leak rate occur.

In accordance with the above description, it will be seen that low pass filter 38' acts on the instantaneous flow rate signal to provide an output corresponding to average system flow, which is system leakage since patient inspiration and expiration over time constitutes a net positive flow of zero. With other enhancements, as described, the system average flow can be viewed as an estimate of leakage flow rate.

The differential amplifier 52 processes the instantaneous flow rate signal and the estimated leak flow rate signal to provide an estimated patient flow rate signal which is integrated and nonzero values of the integral are fed back to module 38' to adjust the estimated leak flow rate signal on a breath by breath basis. The integrator 60 is reset by the IPAP/EPAP state signal via connection 62.

Two circuits are provided which can override the integrator circuit, including end exhalation detector 74 which provides an output to adjust the time constant of low pass Filter 38' and which also is provided as indicated at 86 to reset integrator 60. Gross error detector 82 is also provided to process estimated patient flow rate and to provide an adjustment to estimated leak flow rate under conditions as specified. The output of module 82 also is utilized as an integrator reset signal as indicated at 86. It will be noted that the integrator 60 is reset with each breath of the patient if, during that breath, it is ultimately overridden by module 74 or 82. Accordingly, the multiple reset capabilities for integrator 60 as described are required.

In operation, the system may be utilized in a spontaneous triggering mode, a spontaneous/timed mode or a purely timed mode of operation. In spontaneous operation, decision circuitry 34 continuously compares the instantaneous flow rate with estimated leak flow rate. If the system is in the EPAP state or mode, it remains there until instantaneous flow rate exceeds estimated leak flow rate by approximately 40 cc per second. When this transition occurs, decision circuitry 34 triggers the system into the IPAP mode for 150 milliseconds. The system will then normally remain in the IPAP mode as the instantaneous flow rate to the patient will continue to increase during inhalation due to spontaneous patient effort and the assistance of the increased IPAP pressure.

After the transition to the IPAP mode in each breath, a temporary offset is added to the estimated leak flow rate reference signal. The offset is proportional to the integral of estimated patient flow rate beginning at initiation of the inspiratory breath so that it gradually increases with time during inspiration at a rate proportional to the patient's inspiratory flow rate. Accordingly, the flow rate level above estimated leak flow needed to keep the system in the IPAP mode during inhalation decreases with time from the beginning of inhalation and in proportion to the inspiratory flow rate. With this enhancement, the longer an inhalation cycle continues, the larger is the reference signal below which instantaneous flow would have to decrease in order to trigger the EPAP mode. For example, if a patient inhales at constant 500 cc per second until near the end of inspiration, a transition to EPAP will occur when his flow rate drops to about 167 cc per second after one second, or 333 cc per second after two seconds, or 500 cc per second after three seconds, and so forth. For a patient inhaling a constant 250 cc per second, the triggers would occur at 83, 167 and 250 cc per second at one, two and three seconds into IPAP, respectively.

In this way, the EPAP trigger threshold comes up to meet the inspiratory flow rate with the following benefits. First, it becomes easier and easier to end the inspiration cycle with increasing time into the cycle. Second, if a leak develops which causes an increase in instantaneous flow sufficient to trigger the system into the IPAP mode, this system will automatically trigger back to the EPAP mode after about 3.0 seconds regardless of patient breathing effort. This would allow the volume-based leak correction circuit (i.e., integrator 60) to act as it is activated with each transition to the IPAP mode. Thus, if a leak develops suddenly, there will be a tendency toward automatic triggering rather than spontaneous operation for a few breaths, but the circuit will not be locked into the IPAP mode.

Upon switching back to the EPAP mode, the trigger threshold will remain above the estimated leak flow rate approximately 500 milliseconds to allow the system to remain stable in the EPAP mode without switching again while the respective flow rates are changing. After 500 milliseconds, the trigger threshold offset is reset to zero to await the next inspiratory effort.

The normal state for the circuit is for it to remain in the EPAP mode until an inspiratory effort is made by the patient. The automatic corrections and adjustments to the reference signal are effective to keep the system from locking up in the IPAP mode and to prevent auto-triggering while at the same time providing a high level of sensitivity to inspiratory effort and rapid adjustment for changing leak conditions and breathing patterns.

In the spontaneous/timed mode of operation, the system per forms exactly as above described with reference to spontaneous operation, except that it allows selection of a minimum breathing rate to be superimposed upon the spontaneous operating mode. If the patient does not make an inspiratory effort within a predetermined time, the system will automatically trigger to the IPAP mode for 200 milliseconds. The increased airway pressure for this 200 milliseconds will initiate patent inspiration and provide sufficient time that spontaneous patient flow will exceed the reference signal so that the rest of the cycle may continue in the spontaneous mode as above described. The breaths per minute timer is reset by each trigger to IPAP whether the transition was triggered by the patient or by the timer itself.

In the timed operating mode, all triggering between IPAP and EPAP modes is controlled by a timer with a breath per minute control being used to select a desired breathing rate from, for example, 3 to 30 breaths per minute. If feasible, the selected breathing rate is coordinated to the patients spontaneous breathing rate. The percent IPAP control is used to set the fraction of each breathing cycle to be spent in the IPAP mode. For example, if the breaths per minute control is set to 10 breaths per minute (6 seconds per breath) and the percent IPAP control is set to 33%, then the flow generator will spend, in each breathing cycle, two seconds in IPAP and four seconds in EPAP.

Figure 4:
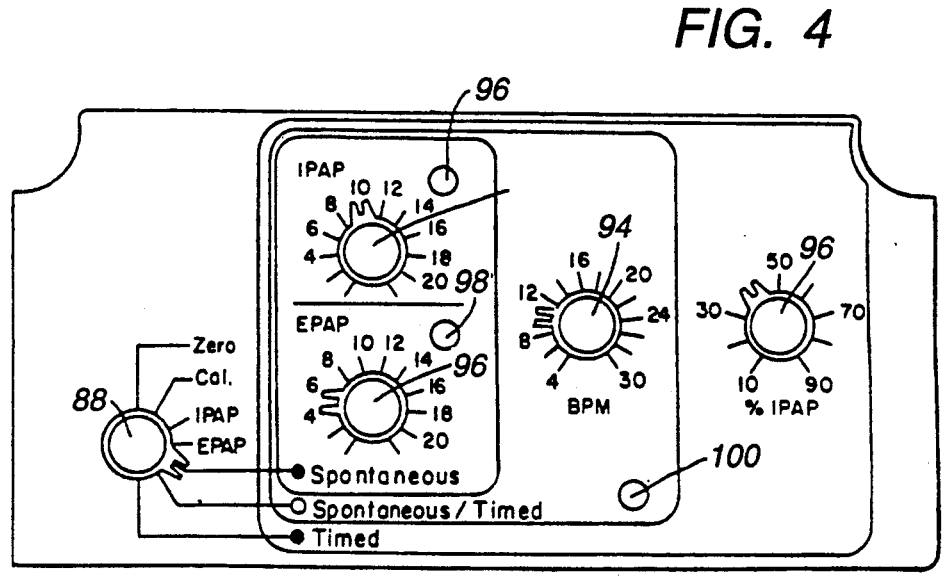
FIG. 4 is a frontal elevation of a control panel for a first embodiment of the apparatus of this invention.

FIG. 4 illustrates control panel for controlling the system above described and including a function selector switch which includes function settings for the three operating modes of spontaneous, spontaneous/ timed, and timed as above described. The controls for spontaneous mode operation include IPAP and EPAP pressure adjustment controls 90 and 92, respectively. These are used for setting the respective IPAP and EPAP pressure levels. In the spontaneous/timed mode of operation, controls 90 and 92 are utilized as before to set IPAP and EPAP pressure levels, and breaths per minute control 94 additionally is used to set the minimum desired breathing rate in breaths per minute. In the timed mode of operation, controls 90, 92 and 94 are effective, and in addition the per cent IPAP control 96 is used to set the time percentage of each breath to be spent in the IPAP mode.

Lighted indicators such as LED's 97, 98 and 100 are also provided to indicate whether the system is in the IPAP or EPAP state, and to indicate whether in the spontaneous/timed mode of operation the instantaneous state of the system is spontaneous operation or timed operation.

Additionally, it may be desirable to provide a flow compensation signal to pressure controller 26 as indicated at 102 in FIG. 2 to compensate for flow resistance inherent in the circuit; a non-rebreathing valve may be utilized in lieu of exhaust port 24 at mask 22, and the like.

Figure 5:
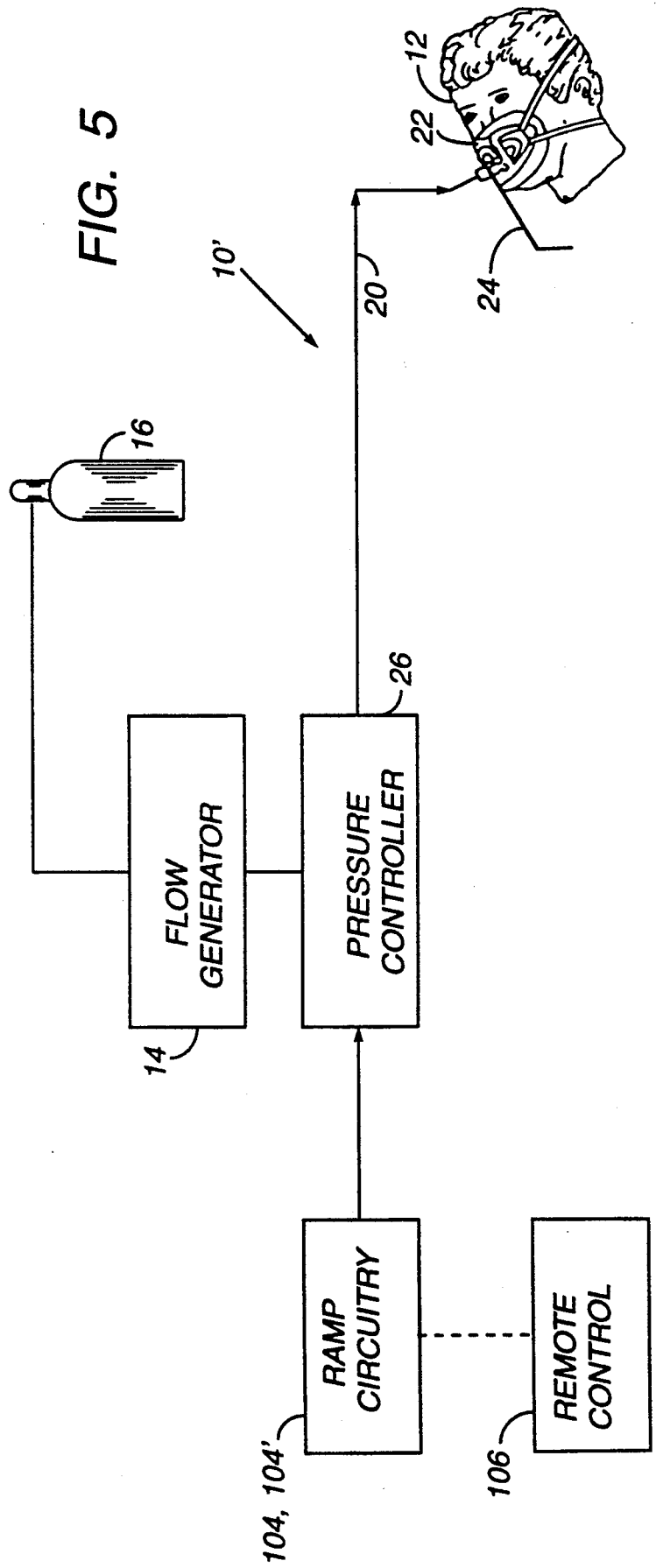
FIG. 5 is a functional block diagram of a further embodiment of an apparatus according to the instant invention.

Turning to FIG. 5, there is depicted a further embodiment of the present invention, herein designated by reference numeral 10'. This embodiment functions substantially as a mono-level CPAP apparatus wherein the pressures of the breathing gas flow supplied to the patients airway is substantially constant except when ramp control circuitry means 104 or 104', described below in connection with FIGS. 7A and 7B, is activated by the patient, through manipulation of a suitable mechanical actuator such as a switch, a button, or the like, provided on the housing of the apparatus 10' or on remote control 106 to produce one or more output pressure "ramp cycles."

Figure 6:
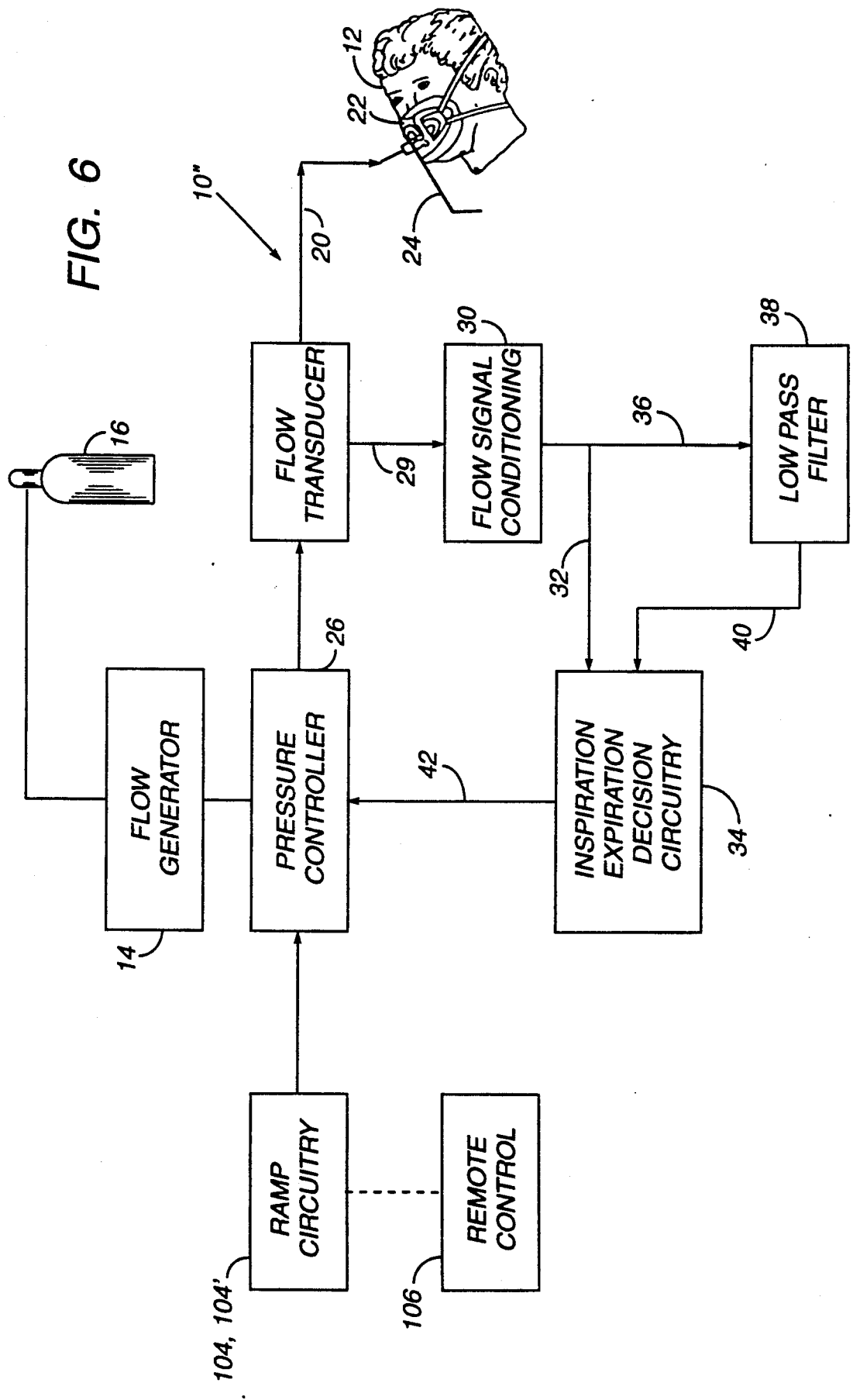
FIG. 6 is a functional block diagram of a further embodiment of an apparatus according to the instant invention.

The embodiment of the instant invention illustrated in FIG. 6 operates much like the embodiment revealed in FIG. 1, i.e., a bi-level CPAP apparatus. Apparatus 10", however, like apparatus 10' shown in FIG. 5, also includes remote control 106 and ramp control circuitry means 104 or 104'.

According to the preferred embodiments, the ramp control circuitry means 104 (FIG. 7A) or 104' (FIG. 7B) provides full prescription pressure on apparatus activation or "start up" and controls the parameters of magnitude, duration and pressure output pattern or "shape" of both the initial ramp cycle and any additional ramp cycles. Unlike other CPAP apparatus having ramp capability wherein a ramp cycle automatically commences upon apparatus start up, apparatus 10' or 10" incorporating ramp control circuiting means 104 or 104' outputs pressure at full prescription pressure (which is preset by the patient's overseeing health care professional) until conscious activation of the initial ramp cycle by the patient. This allows the patient to check for system leaks immediately following start up. Alternatively, ramp control circuitry means 104 or 104' may be so configured such that it automatically commences a ramp cycle upon apparatus startup. The commonality to all embodiments of the ramp control circuitry means being, however, that at least those ramp cycles subsequent to initial ramp cycle be selectively activatable by the patient via means to be described hereinbelow. As will be more fully appreciated from the following, the apparatus 10' or 10" equipped with ramp control circuitry means 104 or 104' permits the patient to not only control the aforesaid parameters of the ramp cycles (which, to provide optimum treatment effectiveness may need to be adjusted daily) but the commencement times of the ramp cycles as well.

Figure 7A:
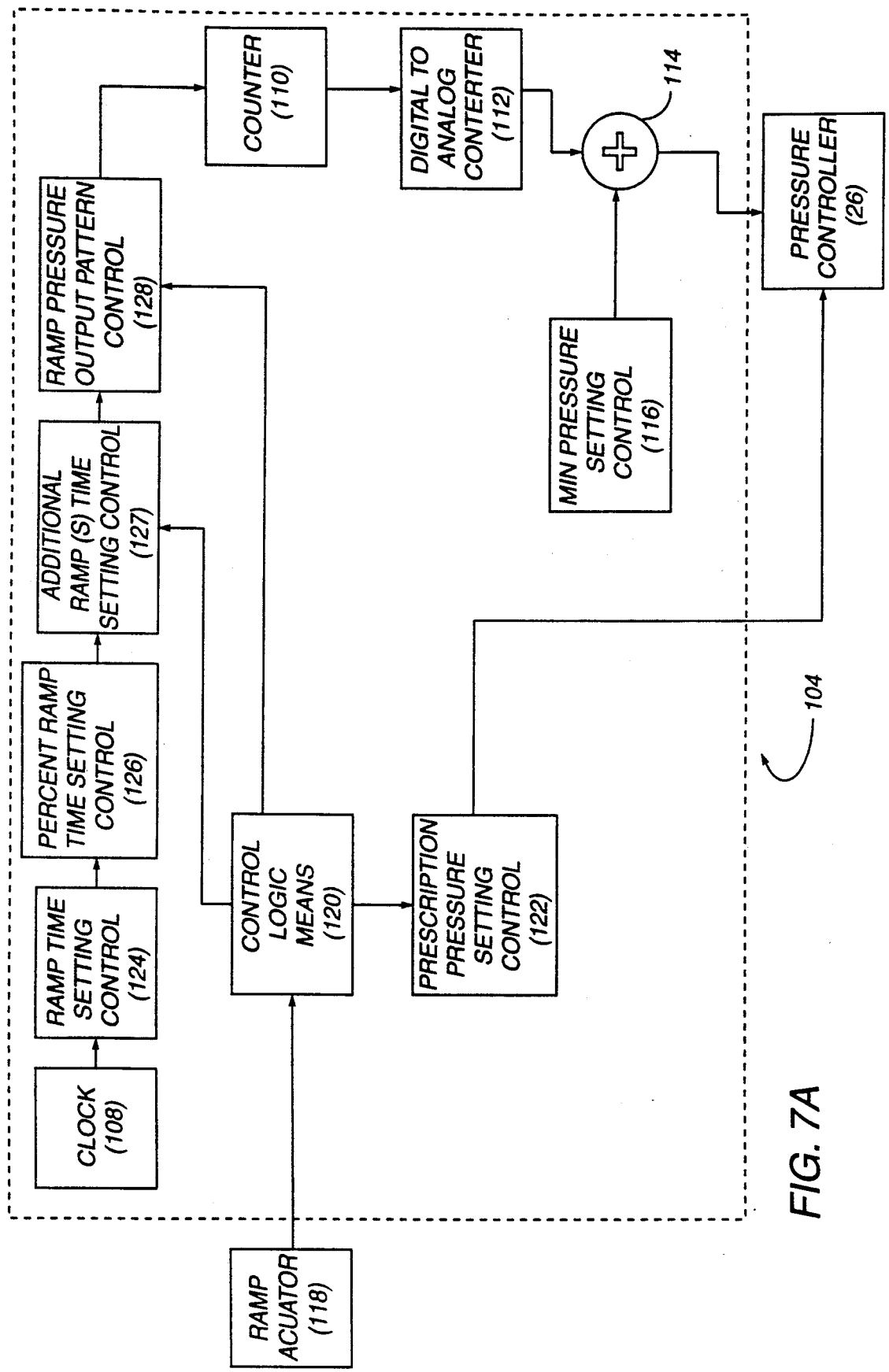
FIG. 7A is a flow diagram of a first embodiment of programmable ramp control circuitry of the instant invention suitable for use in CPAP apparatus.
Figure 7B:
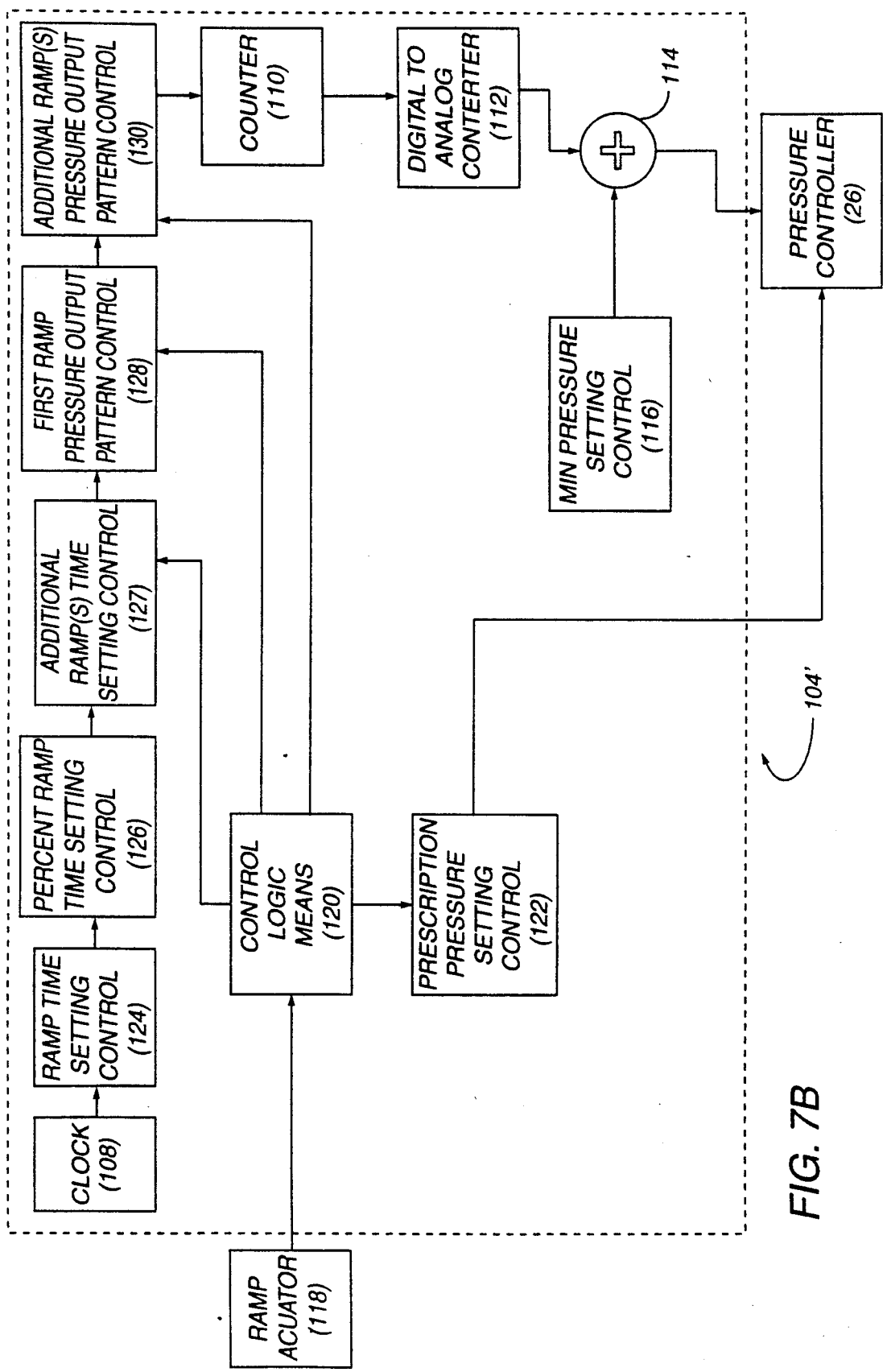
FIG. 7B is a flow diagram of a further embodiment of programmable ramp control circuitry of the instant invention suitable for use in CPAP apparatus.

Turning first to FIG. 7A the ramp cycles produced by the ramp control circuitry means 104 are generated by using a clock 108 to drive a counter 110. The counter 110 increments for each rising edge of the clock 108 and the output of the counter, which is influenced by a number of factors described hereinafter, is transmitted to a digital to analog converter 112. Other suitable means, however, such as a microprocessor may be used in place of digital to analog convertor 112 if desired. The analog output of the converter is added at juncture 114 to the minimum pressure setting that is input via an adjustable minimum pressure setting control 116 and thereafter transmitted to the pressure controller 26 to provide a pressure ramp cycle.

A ramp actuator 118, typically a user-manipulable button, switch, or the like, is operated to effect commencement of a ramp cycle, whether such cycle be the initial or a subsequent cycle. One such ramp actuator is desirably provided on both the apparatus 10' or 10" and the remote control 106. The same arrangement is also preferred for the apparatus power "on/off" actuator. Whether provided on the remote control or apparatus 10' or 10" it is preferred that the power actuator (not shown) be substantially different in physical configuration than that of the ramp actuator such that a patient is provided visual and tactile feedback and can readily and reliably identify and operate the actuators either by sight or sense of touch. For purposes of illustration, both the power actuator and ramp actuator will be understood to be depressible buttons; however, their possible physical manifestations are not intended nor should they be construed to be limited exclusively thereto. Upon depression of the power actuator button, a control logic means 120 selects the patient's prescription pressure as determined by the patient's sleep study as the start-up pressure. The prescription pressure is initially input by the physician or other health care professional into the ramp control circuitry means 104 via a prescription pressure setting control 122 which permits establishment and subsequent adjustment of the magnitude of the prescription pressure. A ramp time setting control 124 such as, for example, a rotary switch or other suitable control, is also provided (preferably internally of the apparatus housing to prevent patient tampering) and it, too, is normally set by the health care professional to establish the appropriate ramp time of the first ramp cycle of the apparatus 10' or 10", i.e., that ramp cycle which is employed when a patient first seeks to fall asleep, such as at bed time. The appropriate ramp time for the first ramp cycle is also determined from data gathered in connection with the patient's sleep study. A typical duration or "ramp time" of the initial ramp cycle may be up to as high as 45 minutes or even more.

As the patient becomes gradually accustomed to using the CPAP apparatus and/or realizes benefits from the CPAP therapy, it is common for the patient to require less time to initially fall asleep when using the apparatus than when the patient first began CPAP treatment. Consequently, when using any CPAP apparatus equipped with the ramp control circuitry means of the present invention, a need occasionally arises for the initial ramp time setting to be adjusted (typically to a lesser duration than that initially set by the health care professional). Since it is oftentimes inconvenient or impractical for the patient to meet with his or her health care professional for necessary readjustments of the ramp time setting control 124, the ramp control circuitry means of the present invention further desirably comprises a percent ramp time setting control 126 that is accessible by the patient and adjustable to produce for the initial ramp cycle a modified initial ramp time that is a fraction of the initial ramp time last established by the health care professional via·ramp time setting control 124. Percent ramp time setting control 126, preferably a rotary switch or the like, is adjustable to produce initial ramp times ranging from a minimum of from about 0 to 20% up to and including a maximum of 100% of the initial ramp time preset by the health care professional.

Frequently, a patient awakens during a period of extended sleep for any number of reasons. And, as is generally the case, the time required for a patient to fall back to sleep once awakened is less than that initially required. To accommodate this particular phenomenon, the ramp control circuitry means 104 (and 104' of FIG. 7B) of the present invention preferably include an additional ramp(s) time setting control 127 that is adjustable to produce in ramp cycles subsequent to the initial ramp cycle (the duration of which is established by the setting of control 124 as modified by the setting of control 126) ramp times ranging from a minimum of from about 0 to 20% of the initial ramp cycle time up to and including a maximum of 100% of the initial ramp cycle time. The ramp circuitry control means 104 and 104' are thus designed such that upon activation of any ramp cycle subsequent to the initial ramp cycle the apparatus 10' or 10" executes a ramp cycle lasting for a duration established by the setting of the additional ramp(s) time setting control 127. Hence, the patient is not only assisted in falling back to sleep by the gradual increase in CPAP pressure but also is more quickly treated by the beneficial prescription pressure once he does again fall asleep due to the generally shorter duration of the subsequent ramp cycle(s) relative to the initial ramp cycle. The additional ramp(s) time setting control 127 is preferably readily accessible by the patient yet not in area where it is likely to be inadvertently bumped or changed.

Looking to FIG. 7A, it is revealed that the ramp control circuitry means 104 also preferably include an adjustable ramp pressure output pattern control 128 for establishing a predetermined pattern of pressure output from pressure controller 26 during progression in a ramp cycle from the minimum ramp pressure set by minimum pressure setting control 116 and the maximum ramp pressure (prescription pressure) set by the prescription pressure setting control 122. In FIG. 7B, the virtual structural and functional equivalent of ramp pressure output pattern control 128 is the first ramp pressure output pattern control 128'. Either of controls 128 or 128' are operable by the health care professional or the patient to establish the selected pattern by which the pressure controller 26 outputs pressurized air during any ramp cycle in the case of ramp control circuitry means 104 or during the first ramp cycle in the case of ramp control circuitry means 104'. Thus, the controls 128 and 128' serve to establish the "shape" of the ramp curve as a function of output pressure versus ramp time. Because of controls 128 and 128', essentially any desired pattern of ramp output pressure may be selected, examples of which will be discussed later by reference to FIGS. 8A, 8B and 8C. In further connection therewith, ramp circuitry control means 104' of FIG. 7B is distinguished from ramp circuitry control means 104 of FIG. 7A by virtue of an adjustable component identified as additional ramp(s) pressure output pattern control 130. The function of this particular control is to enable an operator to form the pressure output pattern of ramp cycles subsequent to the initial ramp cycle into a pattern different therefrom. To illustrate, the initial ramp pattern established by the first ramp pressure output control 128' may be, for example, substantially linear in slope, whereas the subsequent ramp pattern established by the additional ramp(s) pressure output pattern control 130 may be, inter alia, curvilinear or stepped in slope.

The operation of ramp circuitry control means 104 is essentially as follows. Once the apparatus 10' or 10" within which means 104 is incorporated is powered and discharging pressurized air at prescription pressure, a first depression of ramp actuator button 118 results in transmission of a signal to control logic means 120 causing the control logic means to commence a first ramp cycle. When activated, the first ramp cycle effects a drop in output pressure to the minimum pressure setting determined by the position of minimum pressure setting control 116 (typically approximately 2.5 cm $H_2O$) over a period of up to 5 seconds (normal motor-blower run down). Upon reaching the minimum pressure, the output pressure from pressure controller 26 begins to increase and continues to increase for the period of time assigned by the ramp time setting control 124 as modified by percent ramp control 126 in accordance with the predetermined pattern dictated by the ramp pressure output control 128 until the prescription pressure is attained. Thereafter, the output pressure remains at the prescription pressure in the mono-level CPAP apparatus 10' depicted in FIG. 5, while in bi-level CPAP apparatus 10" shown in FIG. 6 the IPAP pressure level remains at the prescription pressure except where the prescription pressure is further modified by the IPAP pressure adjustment control 90 (FIG. 4).

Upon a second or any subsequent depression of the ramp actuator button 118 there is transmitted to the control logic means 120 a signal directing same to commence another ramp cycle whose duration is determined not only by the setting of the ramp time setting control 124 and percent ramp time setting control 126 but also by that of the additional ramp(s) time setting control 127, the influence of such control 127 being selectively overridden by control logic means 120 during the initial ramp cycle. It will be appreciated that the pattern or shape of the pressure output curve of any additional ramp cycle is determined by the setting of ramp pressure output pattern control 128 except that such pattern will be compressed in proportion to the fraction of the initial ramp time chosen by the setting of the additional ramp(s) time setting control 127.

The ramp control circuitry means 104' illustrated in 7B operates essentially identically to its counterpart of FIG. 7A, the primary difference being that ramp control circuitry means 104', via the additional ramp(s) pressure output pattern control 130, enables the pressure pattern of the second and any other additional ramp cycles to differ from that of the initial ramp cycle. As an example, where the first ramp pressure output pattern control 128' may be adjusted so as to produce a substantially linear slope output pressure pattern, the additional ramp(s) pressure output pattern control 130 may be selectively adjusted so as produce a stepped, curved or still other pressure output pattern different from the substantially linear slope of the first ramp cycle, as may be desired or necessary.

Figure 8A:
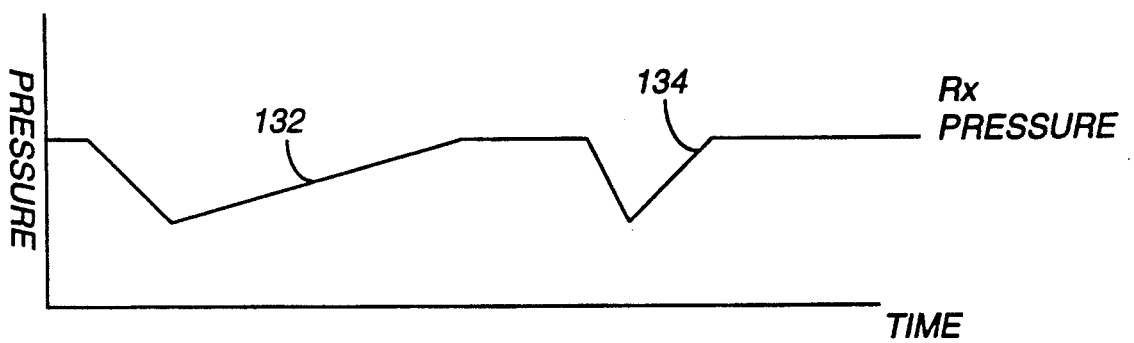
FIGS. 8A, 8B and 8C reveal three examples of typical ramp curve shapes that may be achieved via the programmable ramp circuitry of FIG. 7.
Figure 8B:
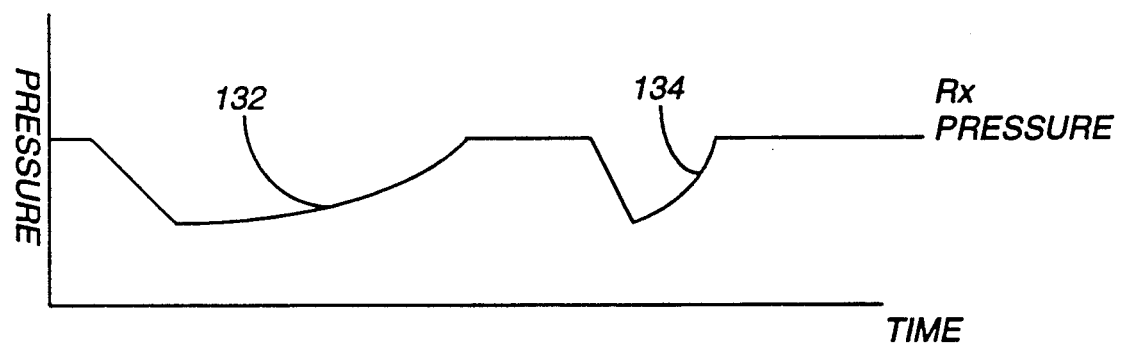
Figure 8C:
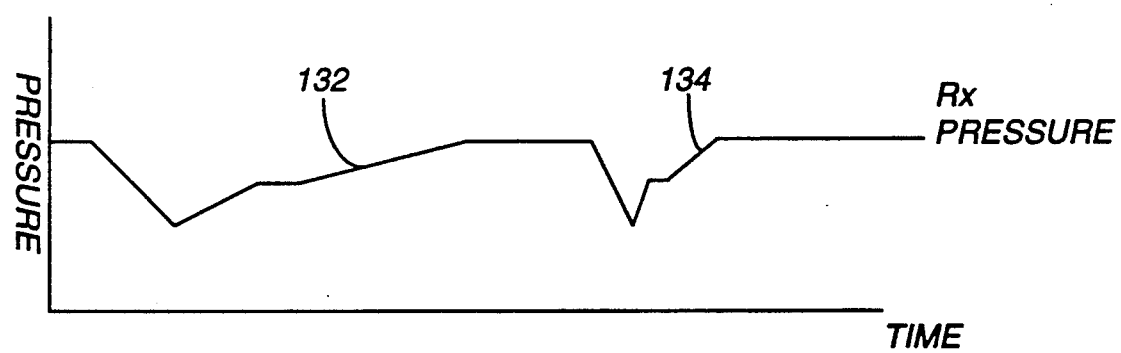

FIG. 8A, 8B and 8C reveal exemplary shapes of pressure output patterns which may be selected for the first 132 and subsequent 134 ramp cycles, namely, substantially linear slope in FIG. 8A, curvilinear in FIG. 8B and stepped in FIG. 8C. It will be appreciated that the pressure output patterns may assume virtually any desired configuration to best suit a particular patient's requirements and, as noted hereabove, the second and subsequent ramp patterns may differ from their associated initial ramp cycles.

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. Apparatus for delivering pressurized gas to the airway of a patient who is breathing in repeated breathing cycles each including an inspiratory phase and an expiratory phase, said apparatus comprising:
    gas flow generator means for providing a flow of said gas;
    means for delivery of said gas flow from said gas flow generator means to the airway of the patient;
    pressure controller means cooperable with said gas flow generator means to provide said gas flow within said means for delivery and within the airway of the patient at selectively variable pressures;
    detector means for continually detecting the rate of flow of said gas between said gas flow generator means and the airway of the patient;
    processor means cooperable with said detector means for continually providing flow rate information of said gas between said gas flow generator means and the airway of the patient, said flow rate information including a first indicia corresponding to the instantaneous flow rate of said gas and a reference indicia approximating the average flow rate of said gas;
    decision means operable to utilize said first indicia and said reference indicia to identify the occurrence of said inspiratory and expiratory phases, said decision means being cooperable with said pressure controller means to control variation of the pressure of said gas flow in response to identification of the occurrence of said inspiratory and expiratory phases; and
    ramp control circuitry means operatively connected to said pressure controller means for effecting (1) a first ramp cycle wherein said gas flow from said pressure controller means is initially output at a first pressure and raises with time to a second pressure, and (2) at least one additional ramp cycle selectively activatable through conscious action of the patient.

2. The apparatus of claim 1 wherein said decision means is operable to adjust said pressure controller means for a higher pressure gas flow within said means for delivery when said first indicia exceeds said reference indicia, and for a lower pressure gas flow within said means for delivery when said first indicia is less than said reference indicia.

3. The apparatus of claim 2 wherein said processor means includes processing elements operable to adjust an existing value of said reference indicia to provide an adjusted value thereof.

4. The apparatus of claim 3 wherein said processing elements include means for processing said first indicia to provide a time average of the flow rate of gas within said means for delivery as a first component of said reference indicia.

5. The apparatus of claim 4 wherein said processing elements further include means for processing said first indicia and said reference indicia to provide a measure of the flow of gas within said means for delivery during a predeterminable time period as a second component of said reference indicia.

6. The apparatus of claim 5 wherein said predeterminable time period is a single complete breathing cycle of the patient including one said inspiratory phase and one said expiratory phase in sequence.

7. The apparatus of claim 6 wherein said processing elements further include means for processing said first indicia and to provide a measure of the value of said first indicia at the end of any said complete breathing cycle by the patient as a third component of said reference indicia.

8. The apparatus of claim 1 further comprising means associated with said ramp control circuitry means for adjusting the magnitude of said first pressure.

9. The apparatus of claim 1 further comprising means associated with said ramp control circuitry means for adjusting the magnitude of said second pressure.

10. The apparatus of claim 9 where said second pressure is a prescription pressure unique to the patient.

11. The apparatus of claim 1 further comprising means associated with said ramp control circuitry means for adjusting the duration of said first ramp cycle.

12. The apparatus of claim 11 further comprising means associated with said ramp control circuitry means for selecting a fraction of an adjusted duration of said first ramp cycle as established by said means for adjusting the duration of said first ramp cycle.

13. The apparatus of claim 12 wherein said means for selecting a fraction of an adjusted duration of said first ramp cycle permits selection of a fraction of said adjusted duration from zero up to and including said adjusted duration.

14. The apparatus of claim 12 further comprising means associated with said ramp control circuitry means for adjusting the duration of said at least one additional ramp cycle.

15. The apparatus of claim 14 wherein said means for adjusting the duration of said at least one additional ramp cycle permits adjustment of the duration of said at least one additional ramp cycle from substantially zero up to and including said adjusted duration.

16. The apparatus of claim 1 further comprising means associated with said ramp control circuitry means for establishing a predetermined pattern of pressure output from said pressure controller means during progression from said first pressure to said second pressure.

17. The apparatus of claim 16 further comprising means associated with said ramp control circuitry means for establishing a pattern of pressure output from said pressure controller means different than said predetermined pattern during said at least one additional ramp cycle.

18. The apparatus of claim 1 further comprising remote control means operable by the patient for selectively activating said apparatus and said ramp control circuitry means.

19. The apparatus of claim 18 where said remote control means includes a first actuator having a first configuration and adapted to be operated by the patient to activate said apparatus and a second actuator having a second configuration substantially different than said first configuration and adapted to activate said ramp control circuitry means, whereby the patient can reliably identify and operate said first and second actuators by sense of touch.

20. Apparatus for delivering pressurized gas to the airway of a patient who is breathing in repeated breathing cycles each including an inspiratory phase and an expiratory phase, said apparatus comprising:
   gas flow generator means for providing a flow of said gas;
   means for delivery of said gas flow from said gas flow generator means to the airway of the patient;
   pressure controller means cooperable with said gas flow generator means to provide said gas flow within said means for delivery and within the airway of the patient at selectively variable pressures;
   detector means for continually detecting the rate of flow of said gas between said gas flow generator means and the airway of the patient;
   processor means cooperable with said detector means for continually providing flow rate information of said gas between said gas flow generator means and the airway of the patient, said flow rate information including a first indicia corresponding to the instantaneous flow rate of said gas and a reference indicia approximating the average flow rate of said gas;
   decision means operable to utilize said first indicia and said reference indicia to identify the occurrence of said inspiratory and expiratory phases, said decision means being cooperable with said pressure controller means to control variation of the pressure of said gas flow in response to identification of the occurrence of said inspiratory and expiratory phases;
   ramp control circuitry means operatively connected to said pressure controller means for effecting (1) a first ramp cycle wherein said gas flow from said pressure controller means is initially output at a first pressure and raises with time to a second pressure, and (2) at least one additional selectively activatable ramp cycle;
   means associated with said ramp control circuitry means for adjusting the magnitude or said first pressure;
   means associated with said ramp control circuitry means for adjusting the magnitude of said second pressure;
   means associated with said ramp control circuitry means for adjusting the duration of said first ramp cycle;
   means associated with said ramp control circuitry means for selecting a fraction of an adjusted duration of said first ramp cycle as established by said means for adjusting the duration of said first ramp cycle;
   means associated with said ramp control circuitry means for adjusting the duration of said at least one additional ramp cycle;
   means associated with said ramp control circuitry means for establishing a predetermined pattern of pressure output from said pressure controller means during progression from said first pressure to said second pressure; and
   remote control means operable by the patient for selectively activating said apparatus and said ramp control circuitry means.

21. The apparatus of claim 20 further comprising means associated with said ramp control circuitry means for establishing a pattern of pressure output from said pressure controller means different than said predetermined pattern during said at least one additional ramp cycle.

22. Apparatus for delivering pressurized gas to the airway of a patient, said apparatus comprising:
   gas flow generator means for providing a flow of said gas;
   conduit means for delivery of said gas flow to the airway of said patient;
   pressure controller means cooperable with said gas flow generator means to provide for flow of said gas within said conduit means and within the airway of said patient at selectively variable pressures;
   ramp control circuitry means operatively connected to said pressure controller means for effecting (1) a first ramp cycle wherein said gas flow from said pressure controller means is initially output at a first pressure and raises with time to a second pressure, and (2) at least one additional ramp cycle selectively activatable through conscious action of said patient; and
   means associated with said ramp control circuitry means for adjusting the duration of said first ramp cycle; and
   means associated with said ramp control circuitry means for selecting a fraction of an adjusted duration of said first ramp cycle as established by said means for adjusting the duration of said first ramp cycle.

23. The apparatus of claim 22 further comprising means associated with said ramp control circuitry means for adjusting the magnitude of said first pressure.

24. The apparatus of claim 22 further comprising means associated with said ramp control circuitry means for adjusting the magnitude of said second pressure.

25. The apparatus of claim 24 wherein said second pressure is a prescription pressure unique to the patient.

26. The apparatus of claim 22 wherein said means selecting a fraction of an adjusted duration of said first ramp cycle permits selection of a fraction of said adjusted duration from zero up to and including said adjusted duration.

27. The apparatus of claim 22 further comprising means associated with said ramp control circuitry means for adjusting the duration of said at least one additional ramp cycle.

28. The apparatus of claim 27 wherein said means for adjusting the duration of said at least one additional ramp cycle permits adjustment of the duration of said at least one additional ramp cycle from substantially zero up to and including said adjusted duration.

29. The apparatus of claim 22 further comprising means associated with said ramp control circuitry means for establishing a predetermined pattern of pressure output from said pressure controller means as said pressure progresses from said first pressure to said second pressure.

30. The apparatus of claim 29 further comprising means associated with said ramp control circuitry means for establishing a pattern of pressure output from said pressure controller means different than said predetermined pattern during said at least one additional ramp cycle.

31. The apparatus of claim 22 further comprising remote control means operable by the patient for selectively activating said apparatus and said ramp control circuitry means.

32. The apparatus of claim 22 wherein said remote control means includes a first actuator having a first configuration and adapted to be operated by the patient to activate said apparatus and a second actuator having a second configuration substantially different than said first configuration and adapted to activate said ramp control circuitry means, whereby the patient can reliably identify and operate said first and second actuators by sense of touch.

33. Apparatus for delivering pressurized gas to the airway of a patient, said apparatus comprising:
gas flow generator means for providing a flow of said gas;
conduit means for delivery of said gas flow to the airway of the patient;
pressure controller means cooperable with said gas flow generator means to provide for flow of said gas within said conduit means and within the airway of the patient at selectively variable pressures;
ramp control circuitry means operatively connected to said pressure controller means for effecting (1) a first ramp cycle wherein said gas flow from said pressure controller means is initially output at a first pressure and raises with time to a second pressure, and (2) at least one additional selectively activatable ramp cycle;
means associated with said ramp control circuitry means for adjusting the magnitude of said first pressure;
means associated with said ramp control circuitry means for adjusting the magnitude of said second pressure;
means associated with said ramp control circuitry means for adjusting the duration of said first ramp cycle;
means associated with said ramp control circuitry means for selecting a fraction of an adjusted duration of said first ramp cycle as established by said means for adjusting the duration of said first ramp cycle;
means associated with said ramp control circuitry mans for adjusting the duration of said at least one additional ramp cycle;
means associated with said ramp control circuitry means for establishing a predetermined pattern of pressure output from said pressure control means during progression from said first pressure to said second pressure; and
remote control means operable by the patient for selectively activating said apparatus and said ramp control circuitry means.

34. The apparatus of claim 33 further comprising means associated with said ramp control circuitry means for establishing a pattern of pressure output from said pressure controller means different than said predetermined pattern during said at least one additional ramp cycle.

* * * * *

UNITED STATES PATENT AND TRADEMARK OFFICE
CERTIFICATE OF CORRECTION

PATENT NO. : 5,239,995

DATED : August 31, 1993

INVENTOR(S) : Mark C. Estes, et al

It is certified that error appears in the above-indentified patent and that said Letters Patent is hereby corrected as shown below:

Column 23, line 29, claim 32, the numeral "22" should be --31 --.

Signed and Sealed this

Twenty-fourth Day of May, 1994

*Attest:*

BRUCE LEHMAN

*Attesting Officer*     *Commissioner of Patents and Trademarks*